(12) United States Patent
Caruso et al.

(10) Patent No.: US 9,090,675 B2
(45) Date of Patent: Jul. 28, 2015

(54) MONOCLONAL ANTIBODIES DIRECTED AGAINST THE HUMAN IMMUNODEFICIENCY VIRUS TYPE 1 (HIV-1) P17 MATRIX (MA) PROTEIN

(75) Inventors: Arnaldo Caruso, Brescia (IT); Giulia Federica Merizzi, Turin (IT); Antonio Soleti, Nichelino (IT)

(73) Assignee: Medestea Research & Production S.p.A., Colleretto Giacosa, TO (IT)

( * ) Notice: Subject to any disclaimer, the term of this patent is extended or adjusted under 35 U.S.C. 154(b) by 0 days.

(21) Appl. No.: 13/637,997

(22) PCT Filed: Mar. 30, 2011

(86) PCT No.: PCT/IB2011/051363
§ 371 (c)(1),
(2), (4) Date: Sep. 28, 2012

(87) PCT Pub. No.: WO2011/121556
PCT Pub. Date: Oct. 6, 2011

(65) Prior Publication Data
US 2013/0028908 A1    Jan. 31, 2013

(30) Foreign Application Priority Data

Mar. 31, 2010    (IT) .............................. TO2010A0257

(51) Int. Cl.
*C07K 16/10*    (2006.01)
*A61K 39/00*    (2006.01)

(52) U.S. Cl.
CPC ....... *C07K 16/1054* (2013.01); *A61K 2039/505* (2013.01); *C07K 2317/33* (2013.01); *C07K 2317/76* (2013.01); *C12N 2740/16011* (2013.01)

(58) Field of Classification Search
CPC ............... C07K 16/1054; C12N 2740/16011
See application file for complete search history.

(56) References Cited

FOREIGN PATENT DOCUMENTS

WO    03016337 A1    2/2003

OTHER PUBLICATIONS

Xiang, J., et al., 1995, Framework residues 71 and 93 fo the chimeric B72.3 antibody are major determinants of the conformation of heavy-chain hypervariable loops, J. Mol. Biol. 253:385-390.*
Bansal, G. P., 2007, a summary of the workshop on passive immunization using monoclonal antibodies for Hiv/Aids, held at the National Institute of Allergy and Infectious Diseases, Bethesda, 10 Mar. 2006, Biol. 35:367-371.*
West, Jr., a. P., et al., 2011, Single-chain Fv-based anti-Hiv proteins: potential and limitations, J. Virol. 86(1):195-202.*
Koefoed, K., et al., 2005, Molecular characterization of the circulating anti-Hiv-1 gp120-specific B cell repertoire using antibody phage display libraries genereated from pre-selected Hiv-1 gp120 binding PBLs, J. Immunol. Methods 297:187-201.*
Maria a. De Francesco, Manuela Baronio, Simona Fiorentini, Costantino Signorini, Carlo Bonfanti, Claudio Poiesi, Mikulas Popovic, Manuela Grassi, Emirena Garrafa, Luisa Bozzo,.
George K. Lewis, Stefano Licenziati, Robert C. Gallo, and Arnaldo Caruso, Hiv-1 matrix protein p17 increases the production of proinflammatory cytokines and counteracts Il-4 activity by binding to a cellular receptor, Jul. 23, 2002, vol. 99, No. 15, pp. 9972-9977, Doi: 10.1073/pnas.142274699 S. Fiorentini, G. De Panfilis, G. Pasolini, C. Bonfanti, & a. Caruso, a Partially Humanized Monoclonal.
Antibody to Human Ifn-y Inhibits Cytokine Effects both in Vitro and in Vivo, Scand. J. Immunol., 2002, vol. 55, pp. 284-292, Blackwell Science Ltd. Simona Fiorentini, Stefania Marsico, Pablo D. Becker, Maria Luisa !Aria, Rosalinda Bruno,.
36, 2008, pp. 4758-4765, Elsevier Ltd.
F. Shang, H. Huang, K. Revesz, H.-C. Chen, R. Herz, and a. Pinter, Characterization of Monoclonal.
Society for Microbiology Matthias Niedrig, Hans-Peter Harthus, Michael Broker, Rob Meloen, Hans Gelderblom, and.
Georg Pauli, Characterization of Murine Monoclonal Antibodies Directed Against the Submembrane Protein p17 of Hiv-1, Hybridoma, 1993, vol. 12, No. 4, pp. 431-439, Mary Ann Liebert Inc.
Deepanker Tewari, Simoy L. Goldstein, Abner L. Notkins and Paul Zhou, cDNA Encoding a Single-.
Chain Antibody to Hiv p17 with Cytoplasmic or Nuclear Retension Signals Inhibits Hiv-1 Replication, the Journal of Immunology, 1998, vol. 161, pp. 2642-2647, the American Association of Immunologists Inc. Reuven Levin, Abner M. Mhashilkar, Tatyana Dorfman, Anatoly Bukovsky, Christy Zani, Jessamyn Bagley, Jorma Hinkula, Mattias Niedrig, Jan Albert, Britta Wahren, Heinrich G.
Gottlinger, and Wayne a. Marasco, Inhibition of Early and Late Events of the Hiv-1 Replication Cycle by Cytoplasmic Fab Intrabodies against the Matrix Protein, p17, Molecular Medicine, 1997, vol. 3, No. 2, pp. 96-110, the Picower Institute Press Veronique Robert-Hebmann, Stephane Emiliani, Frederic Jean, Mariana Resnicoff, Francois.

* cited by examiner

*Primary Examiner* — Jeffrey Parkin
(74) *Attorney, Agent, or Firm* — Robert E. Alderson, Jr.

(57) ABSTRACT

Anti-HIV p17 monoclonal antibodies are described, which are capable of neutralizing the binding between multiple HIV-1 p17 protein variants and the p17R receptor are provided. Pharmaceutical compositions and methods of treatment utilizing these antibodies are also provided.

7 Claims, 5 Drawing Sheets

MONOCLONAL ANTIBODIES DIRECTED AGAINST THE HUMAN IMMUNODEFICIENCY VIRUS TYPE 1 (HIV-1) P17 MATRIX (MA) PROTEIN

CROSS-REFERENCE TO RELATED APPLICATIONS

This application is a National Phase Application of PCT International Application PCT/IB2011/051363, International Filing Date, Mar. 30, 2011, claiming priority to Italian Patent Application No. TO2010A000257, filed Mar. 31, 2010, both of which are hereby incorporated by reference in their entirety.

FIELD OF THE INVENTION

The present invention relates to a monoclonal antibody directed against HIV p17 protein, the said antibody being capable of neutralizing the binding between the p17 protein and the p17 protein receptor (p17R) expressed on the surface of immunocompetent cells.

BACKGROUND OF THE INVENTION p17 protein is known to play an important role in the pathogenesis of AIDS.

p17 is also known to represent the target of neutralizing antibodies directed against HIV-1 and high levels of anti-p17 antibodies are correlated with a slower progression towards AIDS. In addition to its support role in the virus replication, p17 exhibits several immunomodulating properties that could be significant within the context of the viral pathogenesis. p17 was indeed proven to increase the in vitro replication of HIV-1 and affects the activation and differentiation state, in addition to the proliferation ability, of the cells that constitute the target of the virus, such as $CD4^+$ T lymphocytes, NK cells, monocytes, plasmacytoid dendritic cells. The ability of p17 to disrupt the physiological function of various cells of the immune system and to increase the production of pro-inflammatory molecules is very likely a mechanism exploited by the virus to escape the immune response and, at the same time, to create an environment that is more suitable for virus infection and replication. Recently, p17 was also observed to be exported outside the infected cells and it can be detected in the serum of HIV-1-infected patients, remaining in the lymph nodes, also in patients successfully treated with antiretrovirals and thus in the absence of virus replication. Such findings lead to believe that the mechanism of action observed in vitro is also possible in vivo.

Moreover, in previous studies the present inventors demonstrated that p17 protein exerts its biological activity directly by interacting with a specific receptor (p17R) expressed on the surface of several immunocompetent cells. The present inventors also identified an epitope in the N-terminal region of p17 that is involved in the binding with the receptor. The amino acid sequence of such epitope was identified and used for designing a synthetic peptide of 20 amino acids in length, designated as AT20, exemplary of the functional region of p17 from the HIV-1 BH10 isolate (HIV-1 B subtype). The synthetic peptide AT20 coupled with the Keyhole Limpet Hemocyanin (KLH) protein results in the generation of anti-p17 neutralizing antibodies capable of blocking the interaction p17/p17R and, accordingly, its biological activity.

In a subsequent study, the present inventors have also demonstrated that immunization of animals with the full-length p17 BH10 protein or with the synthetic peptide AT20-KLH causes the production of neutralizing sera capable of inhibiting the binding to p17R not only of the p17 BH10 protein but also of a series of African variants of such protein, identified as S75X, S85X, S92X and S012X, respectively (Fiorentini et al., Vaccine 26 (2008) 4758-4765). However, polyclonal antibodies exhibit several drawbacks. First of all, whenever it is desired to produce a polyclonal antibody it is necessary to resort to the immunization of animals. Secondly, the polyclonal antibodies produced at each immunization must be characterized and verified both for their binding and neutralizing properties and for their safety features.

SUMMARY OF THE INVENTION

Such drawbacks have now been overcome thanks to the anti-p17 monoclonal antibody as defined in the claims that follow, the contents of which are an integral part of the technical teachings of the present specification.

The anti-p17 monoclonal antibody subject of the present invention, designated below as "MBA1 antibody", exhibits unexpected properties, as—even though it is a monoclonal—it is endowed with a broad-range neutralizing activity similar to a polyclonal, but on the other hand it does not recognize the neutralizing AT20 epitope recognized instead by the neutralizing sera described in the above-mentioned Fiorentini et al., 2008 reference and by an anti-p17 neutralizing monoclonal previously described and designated as MBS3 (De Francesco et al. Proc Natl Acad Sci USA. 2002 Jul. 23; 99(15):9972-7; WO2003/016337).

DETAILED DESCRIPTION

Figure 1:
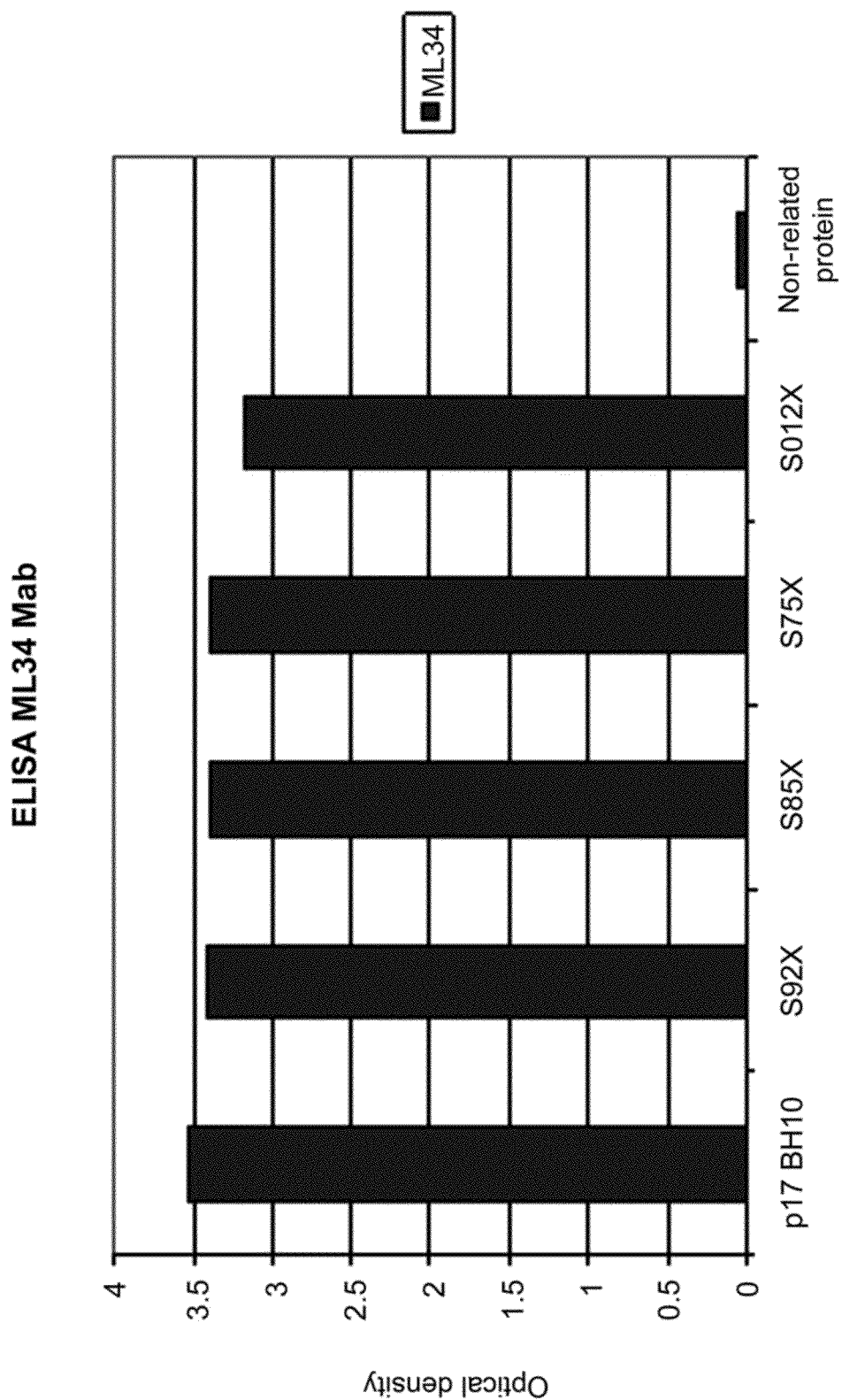
FIG. 1 is a diagram showing binding activity of monoclonal antibodies MBA-1 to HIV p17 BH10, S92X, S85X, S75X and S012X proteins (ELISA assay).

A comparison between the binding and neutralizing properties of the prior art MBS3 antibody and the MBA1 antibody of the present invention is shown in the following experimental section. In particular, a broader range neutralizing activity of the MBA1 antibody of the invention is observed compared to the prior art MBS3 antibody.

Due to its binding and binding neutralization abilities between multiple variants of the HIV-1 p17 protein and the p17R receptor, the MBA1 monoclonal antibody of the invention is particularly suitable to be used as a medicament for the therapeutic treatment of a pathology related to the human immunodeficiency virus. The expression "related to the human immunodeficiency virus" means that the pathology is directly or indirectly caused by said virus. Preferably, the pathology related to the human immunodeficiency virus is selected from the group consisting of acquired immunodeficiency syndrome (AIDS), dementia and lymphoma.

The monoclonal antibody of the invention may be administered in any pharmaceutically acceptable way. For instance, the antibody may be administered by parenteral route, preferably by intravenous injection or slow infusion. Other contemplated administration routes are, for example, the oral, nasal, ophthalmic, rectal or topical routes. Thus, the monoclonal antibody of the invention may be formulated into any suitable dosage form for the intended administration route. In addition to the antibody, which plays the role of the active ingredient, a dosage form includes pharmaceutically acceptable excipients and/or carriers suitable for the intended administration route. The selection of the administration route, the dosage form and the pharmaceutically acceptable carriers and/or excipients are well within the skills of a person of skill in the art. In a particularly preferred embodiment, the monoclonal antibody of the invention is administered by injection. In such a case, the antibody is administered at a dosage within the range from about 0.1 mg/kg to about 100 mg/kg. If the antibody is administered by slow infusion, an infusion period of about 30 minutes to 2 hours may be used for example. The administration is preferably repeated on a monthly, two-monthly or higher basis, for both acute and chronic and intermittent treatments.

A procedure for the manufacture of the MBA1 monoclonal antibody subject of the invention is described in the experimental section below. Further, the studies carried out by the inventors in order to detect the binding and neutralizing properties thereof are reported. The following experimental section is solely provided by way of illustration and non limitation of the scope of the invention as defined in the appended claims.

Experimental Section

1. Immunization 9-week female Balb/c mice were immunized with 25 µg/mouse of the p17 BH10 protein emulsified in Freund's complete adjuvant for the first injection and in Freund's incomplete adjuvant for the last three. The immunizations were performed by intra-peritoneal route at an interval of 7 days. Three days after the last inoculation an intra-caudal immunization was carried out.

2. Cell Fusion and Generation of Hybridomas

The spleen was removed aseptically from each mouse for the recovery of the splenocytes, thus in order to proceed with the fusion to myelomatous cells (NSO), which are genetically deprived of the hypoxanthine-guanine-phosphoribosyltransferase enzyme (HGPRT−). The cell suspension mix so formed was slowly and gently mixed with polyethylene glycol for a few minutes and then transferred into a culture medium containing hypoxanthine, aminopterin and thymidine (HAT medium) in 96-well plates incubated at 37° C. in 5% $CO_2$. The day of the fusion was considered as day 0; the first clones were detected after about three days and the first hybridoma colonies appeared about 15 days after the fusion. The supernatants were then screened in order to assess the possible presence of the antigen-specific antibody. The screening was performed by the ELISA technique. The positive hybridoma colony was collected and cloned into appropriate 96-well plates for the selection of hybridomas that were producing the antibody and for the isolation of a cell line derived from a single clone, thereby obtaining the MBA1 monoclonal antibody capable of reacting against the p17 BH10 protein and the African variants thereof (see below).

3. Production and Characterization of the African Variants of the p17 BH10 Protein HIV-1 genome RNA was isolated from the plasma of Uganda patients by using the viral RNA extraction kit (Qiagen, Milan, Italy). The extract was then retro-transcribed by using the MULV retrotranscriptase (Applera, Monza, Italy) and the resulting cDNA was used as the template to perform a high-fidelity PCR by using Pfu DNA Polymerase. The following primers were used for amplifying partial HIV-1 genome sequences comprising the p17 BH10 gene: UGF1 (5'-GTG CCC GTC TGT TGT GTG A-3', SEQ ID NO:1) and UGR1 (5'-AAT CTT GTG GGG TGG CTC CTT 3', SEQ ID NO:2) for the first step and UGF2 (5'-ACA GGG ACC TGA AAG CGA AAG-3', SEQ ID NO:3) and UGR1 for the second step. The PCR products were purified (Strataprep PCR purification Kit; Stratagene, La Jolla, Calif., United States of America) and inserted into the SrfI-digested pPCR-Script Amp SK(+) cloning vector (Stratagene). Thereafter, both the nucleotide sequences and the orientation of the inserts were verified (CRIBI BMR Genomics Sequence Facility, Padua, Italy). The previously cloned p17 BH10 fragments were further amplified by PCR using the following primers: UGp17For (5'-TAA GGA TCC ATG GGT GCG AGA GCG TCA-3', SEQ ID NO:4) and UGp17Rev (5'-CGG GAA TTC TCA GTA ATT TTG GCT GAC C-3', SEQ ID NO:5) containing the restriction sites BamHI and EcoRI, respectively. The amplified DNA fragment was ligated into the prokaryotic pGEX-4T expression vector (GE Healthcare, Piscataway, N.J., United States of America) in a 10:1 ratio (insert:vector) at 16° C. for 3 hours. The four cloned products, designated as S75X, S85X, S92X and S012X, respectively, were subsequently transformed in *E. coli* BL21 (DE3) cells (Stratagene). The nucleotide sequences thereof were confirmed and the products were expressed by induction with isopropyl-β-D-1-thiogalactopyranoside (IPTG) and purified by glutathione-sepharose 4B beads (GE Healthcare). The S75X, S85X, S92X and S012X and GST proteins were further purified (>98%) by reversed-phase high performance liquid chromatography (HPLC). The absence of contamination with endotoxin in the protein preparations was assessed by the LAL (Limulus amoebocyte lysate) technique (Bio-Whittaker, Walkersville, Me.). Finally, the proteins were biotinylated with biotin-AH-N-hydroxysuccinimide (biotin-AH-NHS, BioSPA, Milan, Italy) for the use thereof in a cytofluorimetric neutralization test.

4. ELISA

The ELISA test was carried out to select hybridomas and clones secreting the antibody capable of recognizing the p17 BH10 protein and the African variants thereof (575X, S85X, S92X and S012X).

Each well of a 96-well plate was incubated with 1 μg/ml of p17 BH10, S75X, S85X, S92X and S012X in a volume of 100 μl PBS, pH 7.2, per well at room temperature overnight. The following day, after several washes in washing buffer (PBS/Tween 20 0.1%), the wells were blocked with 200 μl PBS/BSA 3% per well for 1 hour at 37° C. and subsequently incubated with the cell supernatants to be tested for 1 hour at 37° C. After 4 washes, a goat secondary anti-mouse antibody labeled with HRP enzyme (Thermo Scientific, Waltham, Mass.) was added, which allowed for the development thereof by acting on the OPD substrate (Sigma-Aldrich, St Louis, Mo.). The reading of the optical density was performed by using an automated reader at a wavelength of 492 nm.

5. Western Blot

For a more detailed confirmation of the antibody specificity against the p17 BH10 protein and the African variants thereof, the supernatant of the selected hybridoma was tested by the Western Blot technique, which allows to verify the binding of the antibody to the denatured protein. First of all, the proteins were subjected to a high temperature, for the denaturation thereof, and to a SDS-PAGE electrophoresis.

The latter technique allows the denatured proteins to run in a polyacrylamide gel according to their size, to then be transferred onto a nitrocellulose membrane by the action of an electric field. To reveal the bands corresponding to the proteins, the membrane was stained with Ponceau Red and left to dry. Subsequently, it was subjected to an immunohistochemical assay, by which, after blocking of the specific sites with PBS/BSA 5% and incubation with the sample, it was possible to assess the binding of the MBA1 monoclonal antibody to the proteins (p17 BH10 and African variants thereof) after incubation with a horseradish peroxidase (HRP)-labeled goat secondary anti-mouse antibody and development with the DAB compound (Sigma-Aldrich, St Louis, Mo.).

6. Determination of the Isotype Class of the Monoclonal Antibody

The Isostrip Monoclonal Antibody Isotyping Kit (Saint-Cruz Biotechn) was used to determine the isotype that characterizes the produced and selected MBA1 monoclonal antibody.

7. Cytofluorimetric Neutralization Test for the Monoclonal Antibody

The obtained monoclonal antibody was also subjected to an optimized neutralization test to verify its ability to block the interaction between p17 proteins (BH10 and African variants thereof) and p17R receptor. To this end, the Raji cell line, a neoplastic B lymphocyte line expressing the surface receptor that binds the p17 protein (p17R), was used. Firstly, the antibody was incubated with the p17 BH10 protein or the biotinylated African variants thereof, to allow for the formation of the antigen-antibody complex, and then the Raji cells were added with an incubation for 30' at 4° C. After several washes, a further incubation with streptavidin was carried out to detect, by cytofluorimetric analysis, the possible presence of the protein bound to the p17R surface receptor, not neutralized by the monoclonal antibody.

8. Nucleotide Sequences

The cellular RNA was isolated from the clone secreting the MBA1 monoclonal antibody by using the RNA extraction kit (Qiagen, Milan, Italy). The extract was subjected to retrotranscription by using the High Capacity cDNA Archive Kit (Applied Biosystem) and the resulting cDNA was used as a template to amplify, by PCR, partial sequences encoding the light (Vk) and heavy (Vh) chain variable regions of the monoclonal antibody. The following primers were used to amplify these specific areas: Vk 5' sense: 5'-CAGATCAGATCTCGT-GATGACCCAG-3', SEQ ID NO:6; 3' Vk antisense: 5'-agc-ccgtttgagctccagcttgg-3', SEQ ID NO:7; MuG102, Fd 5' sense: 5'-TGTCCACCTCGAGGTCCAGCTGCAG-CAGTCTGG-3', SEQ ID NO:8; 3' Vh antisense: 5'-gagact-gtcaccggtgtgccttgg-3', SEQ ID NO:9.

The PCR products were cloned into the pGEM-T cloning vector (Promega) by exploiting the "T/A Cloning" method, after which the clones containing the insert were sequenced and analyzed.

The light and heavy chain variable regions of the previously isolated murine Ig gene were then subcloned, after digestion with restriction enzymes (Bgl II and Sac I for Vk; Xho I and Sgr AI for Vh), into expression vector constructs, designated as L122S and L126S, respectively (Fiorentini S et al., Scand J Immunol 55, 284-292, 2002).

9. Results

The generated monoclonal antibody, designated as MBA1, resulted very interesting as to several biochemical-molecular features. The results obtained by the immunoenzymatic ELISA and Western Blot tests demonstrate that MBA1 recognizes the p17 BH10, S75X, S85X, S92X and S012X proteins both in the tertiary conformation and the linear structure. Moreover, this antibody was shown not to recognize the AT20 epitope.

FIG. 1 shows the binding reactivity of the MBA1 antibody towards the different matrix proteins. The diagram shows that the MBA1 monoclonal antibody recognizes and binds the proteins of interest, unlike the non-related protein. These results were also confirmed by Western Blot. The MBA1 monoclonal antibody was actually shown to bind the p17 BH10 protein and the African variants thereof even in the denatured form.

The inventors also identified the antibody isotype of the MBA1 monoclonal antibody, which was shown to be an IgG1/k-chain isotype immunoglobulin.

Figure 2:
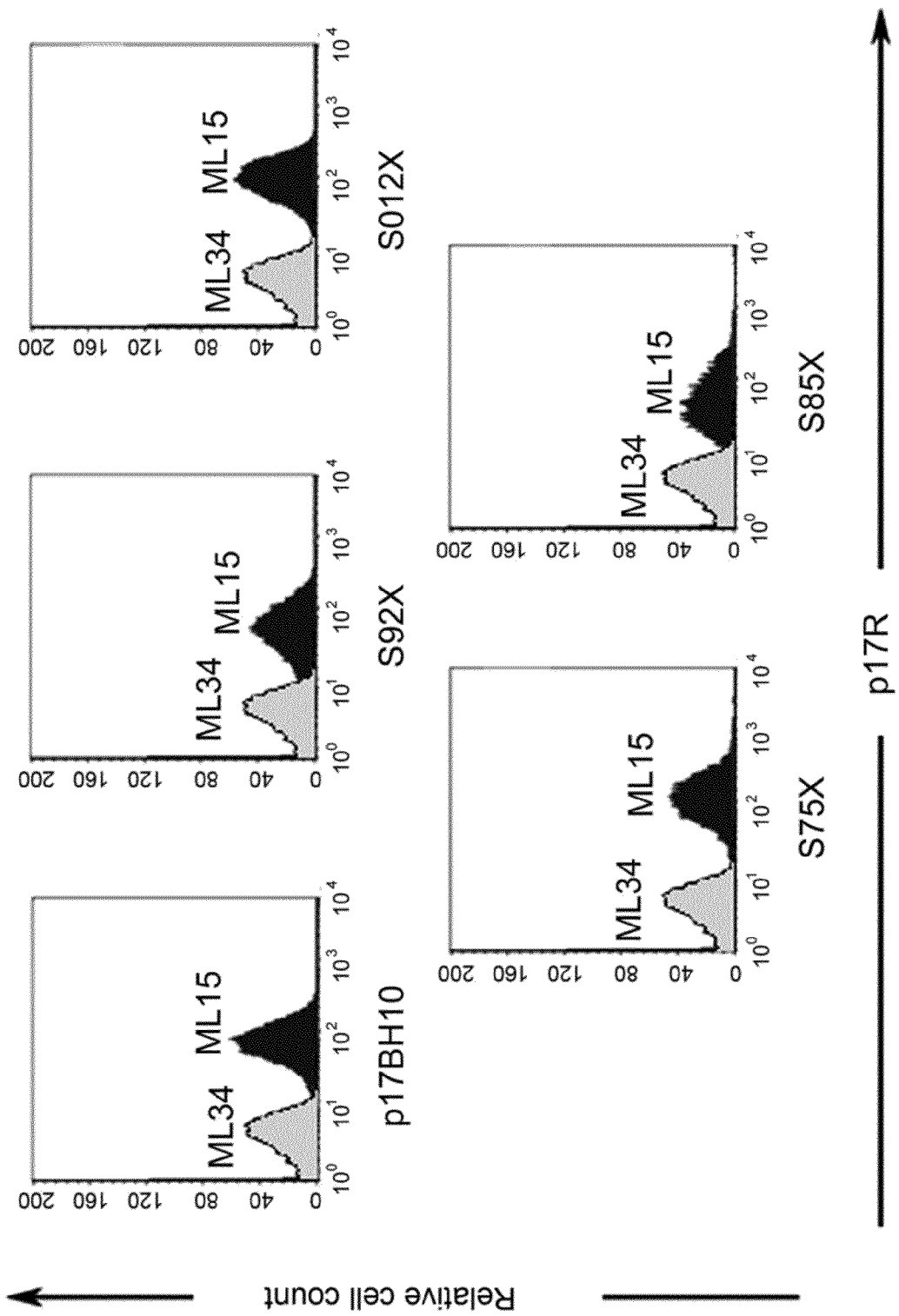
FIG. 2 shows the results of cytofluorimetric analysis of MBA-1 binding ability to HIV p17 BH10, S92X, S85X, S75X and S012X proteins.

A further test was carried out to assess the neutralizing binding ability of the monoclonal antibody of the invention towards the p17 BH10, S75X, S85X, S92X and S012X proteins. By the cytofluorimetric analysis performed on Raji cells, characterized by the presence of p17R on the surface thereof, incubated with the protein complexed to the antibody under examination, it can be noted that none of the cells bind the biotinylated p17 protein or the African variants thereof, as the presence of the monoclonal antibody interferes in a restrictive way, by blocking the interaction p17-p17R (FIG. 2). The inventors verified if the interaction between p17 and its receptor was altered in the presence of another antibody with the same features as the Mab MBA1: in fact, the MBA15 monoclonal antibody selected for this comparison is an IgG1 k-chain immunoglobulin and, as MBA1, it recognizes the different p17 proteins both by ELISA and Western Blot, even if at a different epitope. However, unlike the antibody under examination, MBA15, as FIG. 2 shows, does not alter the interaction between the assayed proteins and their receptor. In fact, the histograms depicted in FIG. 2 show that the p17 BH10 protein and the African variants thereof are able to bind the specific receptor expressed on all of the analyzed Raji cells.

Finally, the inventors carried out a study on the nucleotide sequences encoding the heavy (Vh) and light (Vk) chain variable regions of the MBA1 monoclonal antibody under examination, in order to chimerize the antibody itself. The Vh and Vk variable regions, isolated with specific primers, were inserted into two different expression vector constructs comprising the remaining human antibody regions, in order to finally assemble a chimeric antibody in a single final expression vector. The nucleotide sequences of the heavy chain and light chain variable regions of the MBA1 monoclonal antibody are designated as SEQ ID NO: 10 and SEQ ID NO:11, respectively, in the sequence listing.

Obviously, any monoclonal antibody comprising a heavy chain variable region comprising the amino acid sequence obtainable from the nucleotide sequence SEQ ID NO: 10 and a light chain variable region comprising the amino acid sequence obtainable from the nucleotide sequence SEQ ID NO: 11 falls within the scope of the invention. By virtue of the degeneration of the genetic code, that is the fact that one amino acid may be encoded by several nucleotide triplets, the expression "obtainable from" means that the above-mentioned nucleotide sequences SEQ ID NO:10 and 11 do not have a restrictive meaning.

As an alternative to chimerization, the MBA1 monoclonal antibody of the invention may be manufactured in a humanized form, by conventional techniques well known to the person of skill in the art and therefore do not need further description.

10. Comparative Assessment of the Neutralizing Abilities of MBA-1 and the Neutralizing Abilities of MBS-3 Against the HIV p17 Protein Strain BH10 and the African Variants Thereof.

The monoclonal antibodies MBA-1 (invention) and MBS-3 (prior art), directed against p17 protein, were tested by the Western Blot technique, which allows to verify the binding of the antibody to the denatured and thus linear protein.

At first, the p17 BH10 proteins and the African mutants thereof (S92X, S85X, S75X and S012X) were denatured and subjected to an electrical field according to the SDS-PAGE electrophoresis technique. After the electrophoretic run on a polyacrylamide gel, the proteins were transferred on two different nitrocellulose membranes. To reveal the bands corresponding to the proteins and thereby verify the transfer thereof, the membranes were stained with Ponceau Red and left to dry. The immunohistochemical assay was then carried out, by which, after blocking of the specific sites with PBS/BSA 5% and incubation of the two membranes, each with one of the two monoclonal antibodies to be tested (MBA-1 and MBS-3), it was possible to assess the binding of the antibodies to the proteins (p17 BH10 and African variants thereof) after incubation with a HRP-labeled goat secondary anti-mouse antibody and development on an X-ray film (chemiluminescence).

Monoclonal antibodies MBA-1 and MBS-3 were also subjected to an optimized neutralization test to verify their ability to block the interaction between the p17 BH10 proteins and African variants and their cellular receptor (p17R).

Raji cells, a neoplastic B lymphocyte line expressing the surface receptor that binds the p17 protein (p17R), were used.

Each antibody was incubated with the p17 BH10 protein or the biotinylated African variants thereof, in order to allow for the possible formation of the antigen-antibody complex, which was then incubated with the Raji cells for 30 minutes at 4° C. After several washes, a further incubation with streptavidin was carried out to detect, by cytofluorimetric analysis, the possible presence of the protein bound to the surface receptor, not neutralized by the monoclonal antibody.

The immunoenzymatic test, to which the monoclonal antibodies under examination (MBA-1 and MBS-3) were subjected, showed the attainment of different results for the two antibodies.

Figure 3:
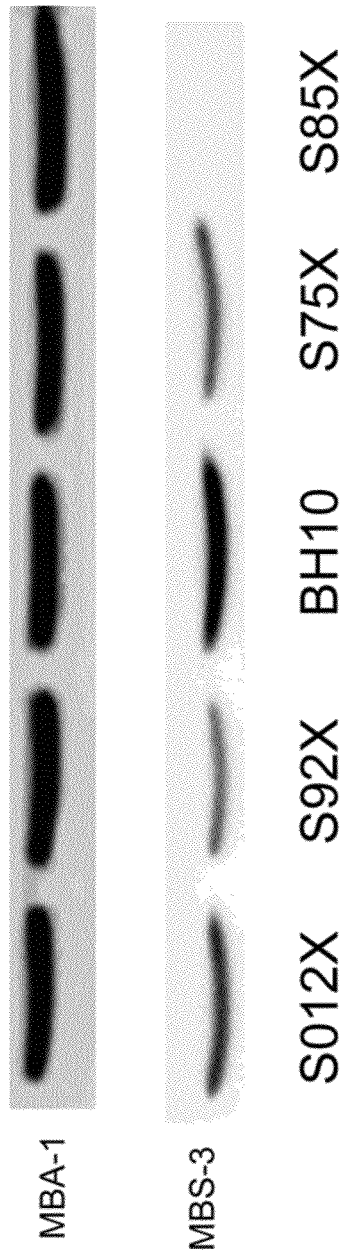
FIG. 3 shows the results of Western blot analysis of MBA-1 binding affinity to HIV p17 BH10, S012X, S92X, S75X and S85X proteins, compared to antibody MBS-3.
Figure 4A:
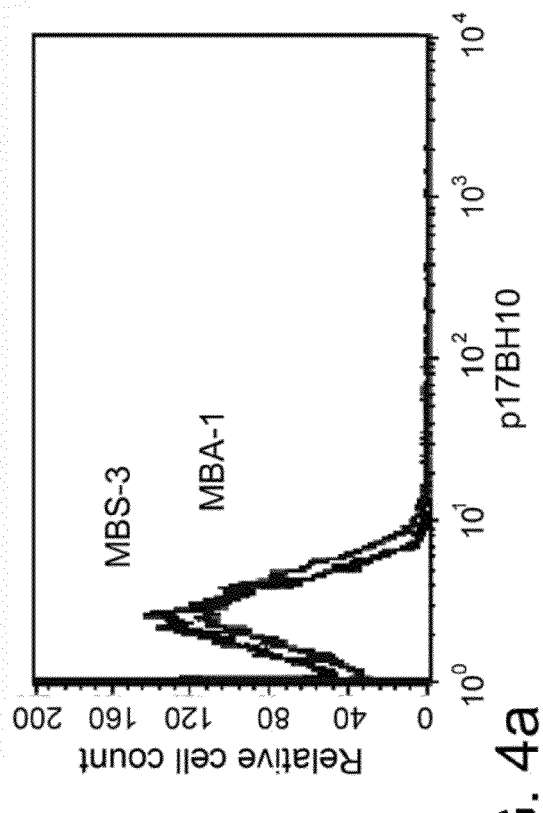
FIGS. 4a-e show the results of cytofluorimetric analysis of MBA-1 neutralizing ability toward HIV p17 BH10, S75X, S85X, S92X and S012X proteins, compared to antibody MBS-3.
Figure 4C:
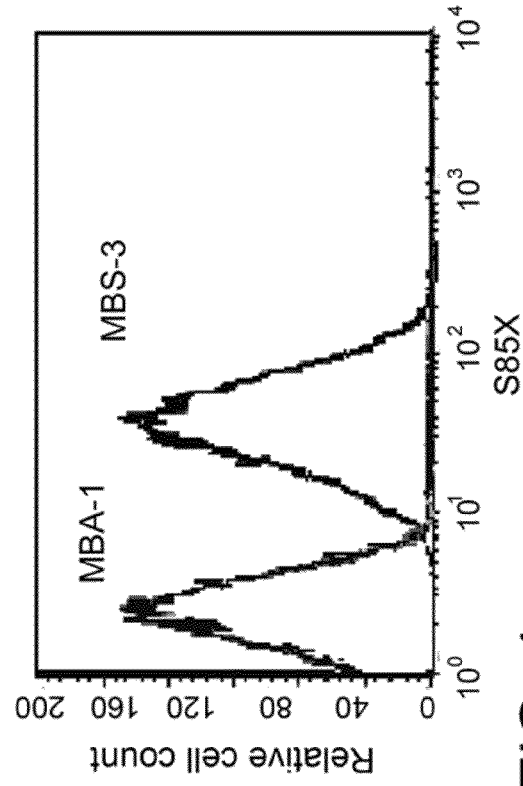
Figure 4B:
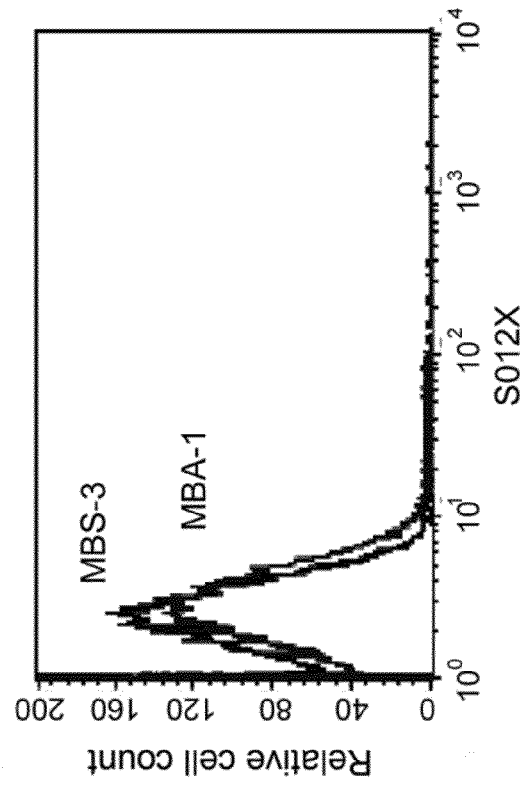
Figure 4E:
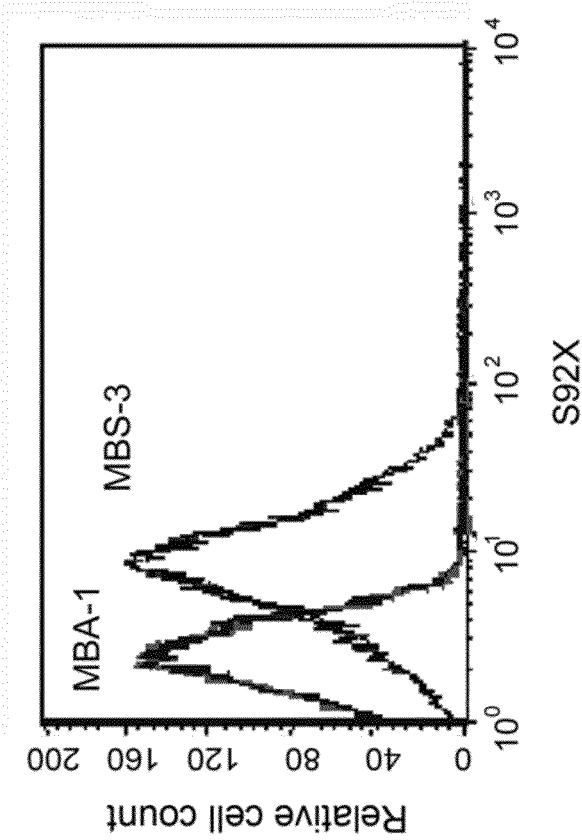
Figure 4D:
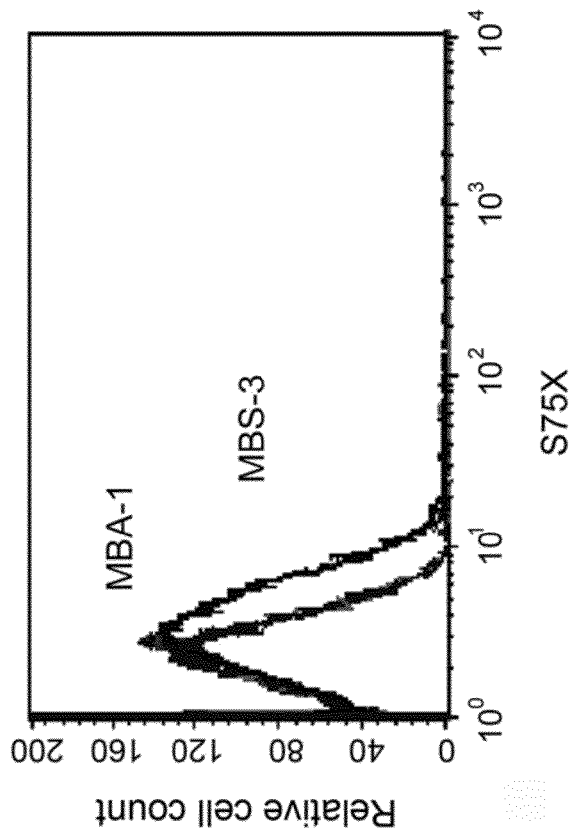

As shown in FIG. 3, with the Western Blot technique, the monoclonal antibody MBA-1 bound all the denatured p17 BH10, S75X, S85X, S92X and S012X proteins with the same affinity. In contrast, MBS-3 bound the p17 BH10 protein and its variants S75X, S92X and S012X with different affinities; instead, the S85X variant was not recognized.

The cytofluorimetric test was performed to verify the ability of two monoclonal antibodies, MBA-1 and MBS-3, to neutralize the binding of the p17 BH10, S75X, S85X, S92X and S012X proteins to the cellular receptor. All the assayed p17 proteins were able to bind p17 receptor expressed on all the Raji cells (FIGS. 4a-e). Adding MBA-1 antibody to the p17 proteins completely inhibited their ability of interacting with the cellular receptor. In contrast, MBS-3 monoclonal antibody blocked completely the interaction between the proteins p17 BH10 and S012X and partially between the proteins S75X and S92X and p17 receptor expressed on the Raji cells. The same antibody was not able to block the interaction between the S85X variant and p17 cellular receptor (FIGS. 4a-e).

The invention claimed is:

1. An isolated monoclonal antibody (mAb) that binds specifically to the human immunodeficiency virus type 1 (HIV-1) p17 matrix (MA) protein wherein said antibody comprises a heavy chain variable region ($V_H$) encoded by the nucleic acid sequence of SEQ ID NO:10 and a light chain variable region ($V_L$) encoded by the nucleic acid sequence of SEQ ID NO:11.

2. The monoclonal antibody of claim 1, comprising a whole immunoglobulin (Ig).

3. The monoclonal antibody of claim 2, comprising an immunoglobulin of the IgG class.

4. The monoclonal antibody of claim 3, comprising an immunoglobulin of the isotype IgG1/k-chain.

5. The monoclonal antibody of claim 1, comprising a Fab fragment.

6. The monoclonal antibody of claim 1, comprising a chimeric antibody.

7. The monoclonal antibody of claim 1, wherein said antibody is humanized.

* * * * *

SEQUENCE LISTING

```
<160> NUMBER OF SEQ ID NOS: 11

<210> SEQ ID NO 1
<211> LENGTH: 18
<212> TYPE: DNA
<213> ORGANISM: artificial
<220> FEATURE:
<223> OTHER INFORMATION: UGF1 primer

<400> SEQUENCE: 1
gtgcccgtct gttgtgtg                                                 18

<210> SEQ ID NO 2
<211> LENGTH: 21
<212> TYPE: DNA
<213> ORGANISM: artificial
<220> FEATURE:
<223> OTHER INFORMATION: UGR1 primer

<400> SEQUENCE: 2
aatcttgtgg ggtggctcct t                                             21

<210> SEQ ID NO 3
<211> LENGTH: 21
<212> TYPE: DNA
<213> ORGANISM: artificial
<220> FEATURE:
<223> OTHER INFORMATION: UGF2 primer

<400> SEQUENCE: 3
acagggacct gaaagcgaaa g                                             21
```

```
<210> SEQ ID NO 4
<211> LENGTH: 27
<212> TYPE: DNA
<213> ORGANISM: artificial
<220> FEATURE:
<223> OTHER INFORMATION: UGp17For primer

<400> SEQUENCE: 4
taaggatcca tgggtgcgag agcgtca                                    27

<210> SEQ ID NO 5
<211> LENGTH: 28
<212> TYPE: DNA
<213> ORGANISM: artificial
<220> FEATURE:
<223> OTHER INFORMATION: UGp17Rev primer

<400> SEQUENCE: 5
cgggaattct cagtaatttt ggctgacc                                   28

<210> SEQ ID NO 6
<211> LENGTH: 25
<212> TYPE: DNA
<213> ORGANISM: artificial
<220> FEATURE:
<223> OTHER INFORMATION: Vk 5' sense primer

<400> SEQUENCE: 6
cagatcagat ctcgtgatga cccag                                      25

<210> SEQ ID NO 7
<211> LENGTH: 23
<212> TYPE: DNA
<213> ORGANISM: artificial
<220> FEATURE:
<223> OTHER INFORMATION: 3' Vk antisense primer

<400> SEQUENCE: 7
agcccgtttg agctccagct tgg                                        23

<210> SEQ ID NO 8
<211> LENGTH: 33
<212> TYPE: DNA
<213> ORGANISM: artificial
<220> FEATURE:
<223> OTHER INFORMATION: MuG102, Fd 5' sense primer

<400> SEQUENCE: 8
tgtccacctc gaggtccagc tgcagcagtc tgg                             33

<210> SEQ ID NO 9
<211> LENGTH: 24
<212> TYPE: DNA
<213> ORGANISM: artificial
<220> FEATURE:
<223> OTHER INFORMATION: 3' Vh antisense primer

<400> SEQUENCE: 9
gagactgtca ccggtgtgcc ttgg                                       24

<210> SEQ ID NO 10
<211> LENGTH: 351
<212> TYPE: DNA
<213> ORGANISM: SCID mouse

<400> SEQUENCE: 10
```

```
gtccacctcg aggtccagct gcagcagtct ggacctgagc tgaagaagcc tggagagaca      60
gtcaagatct cctgcaaggc ttctgtgtat accttcacag aatatccaat acactgggtg     120
aagcaggctc caggaaaggg tttcaagtgg atgggctgga taaacaccta ctctggagag     180
ccaacatatg ctgacgactt caagggacgg tttgccttt ctttggaaac ctctgccagc      240
actgcctatt tgcagatcaa cagcctcaaa aatgaggaca cggctacata tttctgtgcg     300
agtctgggac gggactactg gggccaaggc caaggcacca ctctcacagt c              351

<210> SEQ ID NO 11
<211> LENGTH: 337
<212> TYPE: DNA
<213> ORGANISM: SCID mouse

<400> SEQUENCE: 11
gacatcgtga tgacccagca gactccactc actttgtcga ttaccattgg acaaccagcc      60
tccatctctt gcaagtcaag tcagagcctc ttagatagtg atggaaagac atatttgaat     120
tggttgttac agaggccagg ccagtctcca aagcgcctaa tttattggat gtctaaactg     180
gactctggag tccctgacag gttcactggc agtggatcag ggacagattt cacactgaaa     240
atcagcagag tggaggctga ggatttggga gtttattatt gttggcaagg tacacatttt     300
ccgtggacgt tcggtggagg caccaagctg gagctca                              337
```